United States Patent [19]

Yokotsuka et al.

[11] 3,932,671

[45] Jan. 13, 1976

[54] PROCESS FOR PRODUCING PROTEIN HYDROLYZATE

[75] Inventors: Tamotsu Yokotsuka, Nagareyama; Takashi Iwaasa, Noda; Tadao Okami, Chiba; Minoru Noda, Kamagaya; Mitsuharu Fujii, Noda, all of Japan

[73] Assignee: Kikkoman Shoyu Co., Ltd., Japan

[22] Filed: Mar. 20, 1973

[21] Appl. No.: 342,982

[30] Foreign Application Priority Data

Mar. 27, 1972 Japan.............................. 47-29825

[52] U.S. Cl. ........................ 426/7; 426/18; 426/43; 426/46; 426/49; 426/59; 426/61; 426/650; 195/29
[51] Int. Cl.² .............................................. A23B 4/12
[58] Field of Search ............... 426/43, 7, 52, 49, 56, 426/46, 59, 60, 61, 42, 18, 55, 650; 195/29

[56] References Cited
UNITED STATES PATENTS

| | | | |
|---|---|---|---|
| 3,364,034 | 1/1968 | Hoersch et al. | 426/18 |
| 3,443,969 | 5/1969 | Narcajima | 426/60 |
| 3,495,991 | 2/1970 | Mogi et al. | 426/46 |
| 3,689,277 | 9/1972 | Sfat et al. | 426/46 X |
| 3,761,353 | 9/1973 | Noe et al. | 426/52 X |

Primary Examiner—Raymond N. Jones
Attorney, Agent, or Firm—Cushman, Darby & Cushman

[57] ABSTRACT

A protein hydrolyzate having a high free amino acid content and an excellent flavor can be obtained when salt-resistant lactic acid bacteria are additionally used in the absence or presence of at most 12 percent by weight of sodium chloride based on a volume of an aqueous medium in obtaining the protein hydrolyzate from proteinaceous materials by hydrolysis with proteolytic enzymes.

15 Claims, No Drawings

PROCESS FOR PRODUCING PROTEIN HYDROLYZATE

This invention relates to a process for producing protein hydrolyzates containing increased amount of free amino acids and hence having an improved flavor by additionally utilizing salt-resistant lactic acid bacteria in producing protein hydrolyzates from proteinaceous materials with proteolytic enzymes.

The protein hydrolyzate is known to have extensive uses in various fields such as food industry and pharmaceutical industry. When a protein hydrolyzate is destined for use especially as a seasoning or as a material for seasonings in food industry, there is a strong demand for a product having a high content of free amino acids such as glutamic acid which, among others, has a pronounced flavor enhancing effect.

As is well known to the art, although hydrolysis of proteinaceous materials are generally conducted by either an acid process or an enzymatic process utilizing a proteolytic enzyme preparation or an aspergillus mold culture, the latter process is superior in product quality. However, it is also known to the art that the enzymatic process utilizing a proteolytic enzyme preparation will give a hydrolyzate in which the ratio of free amino acids to total solubilized nitrogen in the hydrolyzate of protein materials (this ratio is hereinafter referred to as free amino acid ratio) is low. It is conceivable, therefore, that in order to attain sufficient splitting of proteinaceous materials by the method of enzymatic hydrolysis, it is necessary to use a proteolytic enzyme having a wide range of substrate specificities or a great variety of enzymes having different substrate specificities among them. However, since ordinary enzyme preparations contain neither such an enzyme of broad-range substrate specificity nor a great variety of enzymes in amounts sufficient for practical use, the low free amino acid ratio has been considered as a defect of the enzymatic hydrolysis.

It is further known that, as compared with the abovesaid process utilizing a proteolytic enzyme, a relatively high free amino acid ratio is attained by a so-called koji process, a variety of the enzymatic process, whereby a proteinaceous material is hydrolyzed by means of "koji" obtained by inoculation and cultivation of an aspergillus mold capable of producing proteolytic enzymes on the protein material as substrate, as in the brewing of soy. The free amino acid ratio of the product obtained by such a method is also not quite satisfactory.

As a result of extensive investigations to eliminate aforesaid disadvantages, the present inventors found that the salt-resistant lactic acid bacteria isolated from a soy mash or other sources do not exhibit hydrolyzing effect in the presence of sodium chloride of high concentrations, as in the case of soy brewing, upon the partial hydrolyzate of protein (peptides and the like not hydrolyzable with ordinary proteolytic enzymes) contained in protein hydrolyzate produced by use of proteolytic enzymes, whilst in the absence or presence of at most 12 percent by weight of sodium chloride based on a volume of an aqueous medium they exhibit a powerful hydrolyzing effect upon said partial hydrolyzate to increase markedly the free amino acid content of the protein hydrolyzate. Based on this novel finding, the present invention has been accomplished.

An object of this invention is to provide a process for producing protein hydrolyzate, characterized by increasing the free amino acid content.

Another object of this invention is to provide a process for producing protein hydrolyzates containing an increased amount of free amino acids and hence having an improved flavor.

Other objects and advantages of this invention will become apparent from the following description.

The process of this invention comprises utilizing salt-resistant lactic acid bacteria in the absence or presence of at most 12 percent by weight of sodium chloride based on a volume of an aqueous medium in producing protein hydrolyzates from proteinaceous materials by hydrolysis with proteolytic enzymes. By the process of this invention, it is possible to obtain protein hydrolyzate containing increased amount of free amino acids and hence having an improved flavor.

The invention is explained below in more detail.

The proteinaceous material for use in the process of this invention may be any of the vegetable proteinaceous materials (e.g. soy bean, wheat gluten, etc.), animal proteinaceous materials (e.g. milk casein, fish meal, cattle meat, etc.) and microorganism proteinaceous materials (e.g. yeast, etc.).

Hydrolysis of such materials by use of proteolytic enzymes is effected in an ordinary manner (e.g. K. Mogi, Journal of Fermentation Technology 36, 125 (1958)). Examples include a method whereby a proteinaceous material is subjected to a suitable denaturation treatment (e.g. ibid) and the denatured proteinaceous material is hydrolyzed by addition of a suitable proteolytic enzyme, and a method whereby an aspergillus mold capable of producing a proteolytic enzyme is inoculated and cultured on a denatured proteinaceous material to convert the latter into koji, in which form the hydrolysis is allowed to proceed.

The proteolytic enzyme to be used may be any of those obtained from animal, vegetable, and microbial sources, but preferably selected from those which are heat resistant or resistant to acid and heat, in order to cut down the hydrolysis time of proteinaceous materials.

Examples of individual proteolytic enzymes are those proteolytic enzymes produced by aspergilli (e.g. *Aspergillus oryzae*, *Aspergillus sojae*, etc.) or streptomyces (e.g. *Streptomyces griseus*, etc.), pepsin, papain, etc.

Examples of the salt-resistant lactic acid bacteria for use in this invention to increase free amino acid content of the protein hydrolyzate produced by use of proteolytic enzymes include lactic acid bacteria in soy, such as Pediococcus halophilus, FERM-P No. 1414, ATCC 21786 (The abbreviation "FERM-P" stands for the access number registered by Fermentation Research Institute, Agency of Industrial Science and Technology, 5-chome 8-1, Inage, Chiba-shi, Japan, a public depository of Japan; "ATCC" stands for the access number registered by American Type Culture Collection, 12301, Parklawn Dr. Rockville, Md.), *Pediococcus soyae*, IAM 1673, ATCC 13,621, Pediococcus soyae, IAM 1,681, ATCC 13,622, *Pediococcus soyae*, IAM 1,685, ATCC 13,623, *Tetracoccus soyae*, FERM-P No. 1401, ATCC 21,787; further, *Streptococcus thermophilus*, IAM 1,047 (IAM: Institute of Applied Microbiology, University of Tokyo, Tokyo, Japan), *Streptococcus thermophilis*, ATCC 19,282, *Streptococcus lactis*, IFO 3,434 (IFO: Institute for Fermentation, Osaka, Japan), *Streptococcus lactis* AHU 1,091 (AHU:

Faculty of Agriculture, Hokkaido University, Sapporo, Japan), *Streptococcus lactis*, IID 7,693 (IID: Institute of Medical Science, University of Tokyo, Tokyo, Japan; previous name is Institute for Infectious Diseases), and *Streptococcus lactis*, ATCC 19,435. All of the above-mentioned strains are salt-resistant lactic acid bacteria which are resistant to sodium chloride in a concentration of 10 percent based on a volume of an aqueous medium or higher and can grow in the said sodium chloride solution.

Mycological properties of these salt-resistant lactic acid bacteria are described in detail in the following literature: Nakagawa, A., Kitahara, K., J. Gen. Appl. Microbiol., 5, 95 (1959) for *Pediococcus halophilus;* Kenji Sakaguchi, Bull. Agr. Chem. Soc. Japan, 22, 353 (1958) for *Pediococcus Soyae;* Hakko Kogahu Zasshi, 39, 360 (1961) for *Tetracoccus Soyae;* Bergey's Manual of Determinative Bacteriology, 7th Ed. (1957) for *Streptococcus thermophilus* and *Streptococcus lactis*. Of the above-noted strains, those assigned with accession numbers of IAM are described in JFCC Catalogue of Cultures, Additional Edition 1966 (JFCC; The Japanese Federation of Culture Collection of Microorganisms); strains assigned with accession numbers of IFO, AHU, and IID in JFCC Catalogue of Cultures, Additional Edition 1968; strains assigned with accession numbers of ATCC in ATCC Catalogue of Strains, Ninth Edition 1970. All of these strains are available to the public.

In the process of this invention, it is possible to use, beside the above-noted salt-resistant lactic acid bacteria, all of those which are capable of increasing the free amino acid content of the protein hydrolyzate produced by use of proteolytic enzymes in the absence or presence of at most 12 percent by weight of sodium chloride based on a volume of an aqueous medium. In this case, salt-resistant bacteria which are resistant to sodium chloride in a concentration of 10 percent by weight based on a volume of an aqueous medium or higher and can grow in the said sodium chloride solution are more preferable.

Among the salt-resistant lactic acid bacteria, those isolated from a soy mash are advantageously used, the say nothing of those salt-resistant lactic acid bacteria which are heat resistant.

In order to obtain desired results of using salt-resistant lactic acid bacteria according to this invention, either the bacteria are inoculated into the protein hydrolyzing system and cultured therein or a large amount of cells of the bacteria are added to the system. The inoculation and cultivation of the salt-resistant lactic acid bacteria or the addition of cells thereof can be conducted either before or after substantial termination of hydrolysis of the proteinaceous material with proteolytic enzyme, the choice being made by taking account of the conditions under which the proteinaceous material is hydrolyzed, such as temperature, pH, etc., though usually conducted preferably after substantial termination of the hydrolysis of proteinaceous materials caused by proteolytic enzymes.

In using the salt-resistant lactic acid bacteria in the process of this invention, it is necessary for achieving the objects of this invention that the concentration of sodium chloride in the protein hydrolyzing system be maintained within the range of 0 to 12 percent by weight based on an amount of an aqueous medium. Concrete examples are shown below concerning the experiments conducted to examine relationships between the sodium chloride concentration and free amino acid content in a protein hydrolyzate obtained by use of a proteolytic enzyme when the salt-resistant lactic acid bacteria are inoculated and cultured therein or the bacteria are added thereto to be brought into contact therewith.

EXPERIMENT 1

By use of a proteolytic enzyme preparation obtained from Aspergillus oryzae grown on wheat bran in the form of koji (said preparation being a dried powder of precipitates obtained from an aqueous extract of the wheat bran koji on addition of ethyl alcohol three times in volume), defatted soy bean which had been subjected to denaturation treatment was hydrolyzed in a customary way to obtain a protein hydrolyzate of a total dissolved nitrogen content (TN) of 2.0 percent (W/V), containing 0.86 percent (W/V) of free amino acids in terms of amino nitrogen (AN), the free amino acid ratio (AN/TN) being 0.43. The amino nitrogen was obtained by substracting the ammonium nitrogen measured by Conway micro-diffusion method from the formol nitrogen measured by formol titration. The total dissolved nitrogen was measured by Kjeldahl method (I. Umeda "Shoyu" Sankyo Shuppan Co., Tokyo, 1961, p 138).

The above-obtained protein hydrolyzate was then subjected to heat treatment at 90°C. for 5 minutes to deactivate the proteolytic enzyme and filtered. Sodium chloride was added to the clear filtrate to prepare protein hydrolyzate solutions (pH 6.0) containing sodium chloride in various concentrations as shown in Table 1. Pediococcus soyae IAM 1673 (ATCC 13621) was inoculated into each solution and allowed to undergo stationary culture at 20° to 30°C. for 10 days, when the percentage increase in free amino acid content (AN) was determined to obtain the results as shown in Table 1. The percentage increase in free amino acid content was found to be substantially the same after the protein hydrolyzate solution (in which the salt-resistant lactic acid bacterium had been inoculated and cultured) had been left standing for longer period of time.

Table 1

| NaCl concentration, % (W/V) | 0 | 3.5 | 7.0 | 10.5 | 12.0 | 13.0 | 14.0 | 15.0 |
|---|---|---|---|---|---|---|---|---|
| Percentage increase in free amino acid content, % | 22.5 | 16.0 | 18.0 | 20.0 | 16.0 | 4.0 | 4.0 | 2.0 |

EXPERIMENT 2

In a protein hydrolyzate (clear solution) obtained in the same manner as in Experiment 1, was dissolved sodium chloride to prepare protein hydrolyzate solutions (pH 6.0) containing sodium chloride in various concentrations as shown in Table 2. To each solution were added cells of Pediococcus soyae IAM 1673 (ATCC 13621) which had been cultured at 30°C. for 120 hours in a medium comprising 1.0 percent (W/V) of glucose, 0.5 percent (W/V) of peptone, and 0.5 percent (W/V) of yeast extract and containing sodium chloride in the same concentration as that shown in Table 2, the number of cells added being $10^8$ per milliliter of the solution. Reaction was allowed to proceed at 45°C. for 5 hours while the solution being stirred mildly to ensure contact with the cells. Then, the percentage increase in free amino acid content (AN) was measured to obtain the results as shown in Table 2. The percentage increase in free amino acid content was found to be substantially the same after the protein hydrolyzate solution (in which the salt-resistant lactic acid bacterium had been added) had been left standing for longer period of time.

phenomena are observed when salt-resistant lactic acid bacteria were inoculated into a reaction mixture before substantial termination of hydrolysis and cultured therein or when cells of the bacteria were mixed and contacted with a reaction mixture before substantial termination of hydrolysis.

In the process of this invention, suitable culture conditions for the salt-resistant lactic acid bacteria inoculated into a reaction mixture before substantial termination of hydrolysis or into a hydrolyzate after substantial termination of hydrolysis are such that pH is generally 5 to 8, preferably 5.5 to 7.0, the temperature is 15° to 60°C., and the culture time is 1 to 15 days; the culture may be carried out by any of the methods such as agitated culture, aerated culture, and stationary culture.

In the case of mixing and contacting the cells of salt-resistant lactic acid bacteria with a reaction mixture Table 2

| NaCl concentration, % (W/V) | 0 | 3.5 | 7.0 | 10.5 | 12.0 | 13.0 | 15.0 |
|---|---|---|---|---|---|---|---|
| Percentage increase in free amino acid content, % | 19.0 | 18.0 | 17.2 | 18.0 | 16.0 | 4.0 | 2.0 |

EXPERIMENT 3

Percentage increase in the free amino acid content was examined in the same manner as in Experiment 1, except that strains shown in Table 3 were used in place of the Pediococcus soyae IAM 1673 (ATCC 13621) and concentrations of sodium chloride in the protein hydrolyzate solution were as shown in Table 3. The results obtained were as tabulated in Table 3. The percentage increase in free amino acid content was found to be approximately the same as shown in Table 3 after the protein hydrolyzate solution (in which the salt-resistant lactic acid bacterium had been inoculated and cultured) had been left standing for longer period of time.

Table 3

| Name of strain | Percentage increase in free amino acid content (%) Concentration of NaCl, % | | | | |
|---|---|---|---|---|---|
| | 0 | 5 | 10 | 12 | 15 |
| Pediococcus halophilus FERM-P No. 1414 (ATCC 21786) | 25 | 20 | 18 | 13 | 3 |
| Tetracoccus soyae FERM-P No. 1401 (ATCC 21787) | 22 | 20 | 18 | 13 | 2 |
| Streptococcus thermophilus ATCC 19282 | 15 | 15 | 13 | 10 | 0 |
| Streptococcus lactis ATCC 19435 | 14 | 16 | 15 | 11 | 1 |

As is apparent from the above Experiments 1 to 3, when inoculated salt-resistant lactic acid bacteria were cultured in a protein hydrolyzate obtained by use of proteolytic enzymes or when cells of said bacteria were brought into contact with said hydrolyzate by mixing, the free amino acid content of said hydrolyzate will increase only when the concentration of sodium chloride in the hydrolyzate remains within the range from 0 to 12 percent (W/V); no useful result will be obtained when sodium chloride is present in concentrations exceeding the upper limit specified herein. The same before substantial termination of hydrolysis or with the hydrolyzate after substantial termination of hydrolysis, a separate culture of the bacteria becomes necessary. In such a case, the culture medium can be either the aforesaid protein hydrolyzate solution or an ordinary medium for use in culturing lactic acid bacteria. Such a medium comprises, for example, a carbon source such as glucose, fructose, mannose, maltose, or dextrin, a nitrogen source such as peptone, casamino acid, meat extract, or yeast extract, and other ingredients such as inorganic phosphates, inorganic calcium salts, vitamins, growth stimulant substances, and sodium chloride. During the culture, concentration sodium chloride is maintained preferably at 12 percent (W/V) or lower and pH is preferably within the range from 6.0 to 8.0. The culture can be conducted following the general culturing procedure for lactic acid bacteria in such a way that the culture medium is mildly stirred without aeration, or is left standing at 15° to 60°C. for 2 to 7 days to obtain satisfactory result.

On completion of the culture, collection of the cells is carried out according to an ordinary procedure for recovering microorganism cells, including centrifuging, filtration, etc. If necessary, a sterile collection method may be adopted and a step of washing the cells with clean water may be added.

The cells of salt-resistant lactic acid bacteria thus collected are added to a reaction mixture before substantial termination of hydrolysis or to the hydrolyzate after substantial termination of hydrolysis preferably in relatively large amounts so that the number of cells per milliliter of the medium may reach about $10^8$ to $10^{10}$.

After addition of the cells of salt-resistant lactic acid bacteria, the medium is agitated by suitable means to keep good contact with the cells at 15° to 60°C. for 10 to 72 hours, while keeping pH within the range from 5.0 to 8.0 to obtain favorable results.

After the reaction is completed, the reaction mixture as such, or after having been freed from the cells, is concentrated and even pulverized to be used as a seasoning or as a material for food processing.

Thus, according to this invention, the free amino acid ratio (AN/TN) in the protein hydrolyzate shows an increase by 10 to 25 percent in both cases of inoculation and cultivation of salt-resistant lactic acid bacteria and of addition of the cells thereof. Such a high ratio of free amino acids has not been attained by the conventional enzymatic hydrolysis. According to this invention, a protein hydrolyzate having a flavor far superior to that of the conventional product can be easily obtained.

The protein hydrolyzate obtained by the process of this invention is concentrated either directly or after having been freed from the cells, etc., by suitable filtration means. The concentrated hydrolyzate is used as such, or after having been converted into a powder, as a seasoning or as a material in food processing.

Examples are shown below to illustrate the present invention, but the scope of the invention is not limited to the Examples.

EXAMPLE 1

To 4 kg of thermally denatured defatted soy bean, were added 1 kg of wheat bran koji prepared with Aspergillus oryzae in a customary way and 25 liters of tap water. While the mixture being stirred at 55° to 60°C. for 15 hours, hydrolysis was allowed to proceed. Then the hydrolyzed mixture was filtered to obtain a clear solution [TN = 1.01 % (W/V)]. The ratio of amino nitrogen to total nitrogen, i.e. AN/TN, of the solution was 0.42.

To one liter of the hydrolyzate solution, was added sodium chloride to give a concentration of 7.5 percent (W/V). After having been adjusted to pH 6.0 and sterilized at 120°C. for 10 minutes, the hydrolyzate solution was inoculated with 10 ml of a culture liquor prepared by culturing Pediococcus halophilus FERM-P No. 1414 (ATCC 21786), a lactic acid bacterium isolated from soy, in a soy fermentation medium (a diluted solution containing 5.0 % (W/V) of NaCl and 0.4 % (W/V) of TN). The inoculated hydrolyzed solution was subjected to a stationary culture at 30°C. On twelfth day or culture, the hydrolyzate solution showed that AN/TN = 0.52, and percentage increase in free amino acid content was 23.8 percent. The protein hydrolyzate obtained had a flavor far superior to that of conventional product.

The aforesaid protein hydrolyzate was treated and left standing at 30°C. for 12 days in the same manner as mentioned above, except that the above-noted salt-resistant lactic acid bacterium was not inoculated. The free amino acid ratio (AN/TN) of the resulting protein hydrolyzate was not differed from that of the clear hydrolyzate solution immediately after hydrolysis.

EXAMPLE 2

To 500 g of commercial wheat gluten (produced by Shinshin Shokuryo Co.), were added 10 g of a proteolytic enzyme preparation obtained from wheat bran koji prepared with Aspergillus oryzae (said preparation being a dried powder of precipitates obtained from an aqueous extract of the wheat bran koji on addition of ethyl alcohol three times in volume) and 5 liters of tap water. Hydrolysis was allowed to proceed while the mixture being stirred at 55° to 60°C. for 12 hours. Insoluble matters were removed by centrifuging to obtain a clear hydrolyzate solution [TN = 1.15 % (W/V)], which showed AN/TN = 0.41.

After having been adjusted to pH 6.5 and sterilized, one liter of the hydrolyzate solution was inoculated with 10 ml of a culture liquor prepared by culturing Pediococcus soyae IAM 1673 (ATCC 13621) in a liquid medium containing 1.0 percent (W/V) of glucose, 0.5 percent (W/V) of peptone, and 0.5 percent (W/V) of yeast extract. The inoculated hydrolyzate solution was incubated at 25°C. for 2 weeks. The free amino acid ratio (AN/TN) of the hydrolyzate solution rose to 0.49 and the percentage increase of free amino acid content was 19.5 percent. The protein hydrolyzate had an excellent flavor.

The aforesaid protein hydrolyzate was treated and left standing at 25°C. for 2 weeks in the same manner as mentioned above, except that the above-noted salt-resistant lactic acid bacterium was not inoculated. The free amino acid ratio (AN/TN) of the resulting protein hydrolyzate was not differed from that of the clear hydrolyzate solution immediately after hydrolysis.

EXAMPLE 3

In a 2 % (W/V) solution (pH 7.0) of milk casein (produced by Merck Co.), was dissolved a proteolytic enzyme ("Pronase", produced by Kaken Chemical Co.) to provide a concentration of 2,000 units per milliliter. Hydrolysis was allowed to proceed at 45°C. for 10 hours to obtain a hydrolyzate solution [TN = 0.28 % (W/V)] having a free amino acid ratio (AN/TN) of 0.36.

After having been adjusted to pH 6.5 and sterilized, 100 ml of the hydrolyzate solution was inoculated with two platinum-loopful cells of Pediococcus soyae IAM 1685 (ATCC 13623) and stationarily incubated at 30°C. for 10 days. At the end of incubation, the hydrolyzate solution showed a free amino acid ratio (AN/TN) of 0.45 and had an excellent flavor.

The aforesaid hydrolyzate solution was treated and left standing at 30°C. for 10 days in the same manner as mentioned above, except that the above-noted salt-resistant lactic acid bacterium was not inoculated. The free amino acid ratio (AN/TN) of the resulting hydrolyzate solution was not changed from that of the hydrolyzate solution immediately after hydrolysis.

EXAMPLE 4

To one liter of a wheat gluten hydrolyzate solution [TN = 1.15 % (W/V)], which had been obtained in the same manner as in Example 2 and adjusted so as to contain sodium chloride in a concentration of 5.0 percent (W/V), were added cells of Tetracoccus soyae FERM-P No. 1401 (ATCC 21787), which had been cultured in a medium containing 1.0 percent (W/V) of glucose, 0.2 percent (W/V) of meat extract, 0.5 percent (W/V) of casamino acid, and 0.5 percent (W/V) of yeast extract, so that the hydrolyzate solution may contain $10^8$ cells per milliliter. The resulting mixture was stirred at 45°C. for 10 hours to ensure contact of the cells with the hydrolyzate solution. On analysis after the treatment, the hydrolyzate solution showed a free amino acid ratio (AN/TN) of 0.47, the percentage increase in free amino acid content being 14.6 percent. The hydrolyzate solution was freed from the cells, concentrated, and spray-dried to yield 120 g of a powdered seasoning having excellent flavor.

The aforesaid wheat gluten hydrolyzate solution was treated and stirred at 45°C. for 10 hours in the same manner as mentioned above, except that the solution was not contacted with cells of the above-noted salt-resistant lactic acid bacterium. The thus treated hydrolyzate solution showed a free amino acid ratio (AN/TN) not different from that of the clear hydrolyzate solution immediately after hydrolysis.

EXAMPLE 5

To 10 g of fish meal (produced by Taiyo Fishery Co.), were added 10 g of wheat bran koji prepared with Aspergillus oryzae and 100 ml of tap water. After the mixture had been adjusted to pH 6.0, hydrolysis was allowed to proceed with stirring at 55°C. for 24 hours. After having been freed from insoluble matters, the hydrolyzate solution [TN = 0.85 % (W/V)] showed a free amino acid ratio (AN/TN) of 0.32. To the hydrolyzate solution, were added cells of Streptococcus thermophilus IAM 1047, which had been cultured in the same medium as that mentioned in Example 4, so that the hydrolyzate solution may contain $10^8$ cells per milliliter. The resulting mixture was stirred at 50°C. for 6 hours to ensure contact of the cells with the solution. The free amino acid ratio (AN/TN) of the resulting hydrolyzate solution having an excellent flavor was found to have increased to 0.40, the percentage increase in free amino acid content being 25 percent.

The aforesaid protein hydrolyzate solution was treated and stirred at 50°C for 6 hours in the same manner as mentioned above, except that the solution was not contacted with cells of the above-noted salt-resistant lactic acid bacterium. The thus treated protein hydrolyzate solution showed a free amino acid ratio (AN/TN) not different from that of the clear hydrolyzate solution immediately after hydrolysis.

EXAMPLE 6

To 10 g of commercial baker's yeast ("Nitten" dry yeast), were added 10 g of wheat bran koji prepared with Aspergillus oryzae and 100 ml of tap water. After the mixture had been adjusted to pH 6.0, hydrolysis was allowed to proceed at 55°C. for 20 hours. After having been free from insolubles, the resulting hydrolyzate solution [TN = 0.65 % (W/V)] showed a free amino acid ratio (AN/TN) of 0.43.

After having been adjusted to pH 6.5 and sterilized, the hydrolyzate solution was inoculated with a platinum-loopful Tetracoccus soyae FERM-P No. 1401 (ATCC 21787) and incubated at 30°C. for 10 days. The free amino acid ratio (AN/TN) was found to have increased to 0.54, the percentage increase in free amino acid content being 25.6 percent. To the incubated hydrolyzate solution, was added sodium chloride so that the concentration thereof may become 18 percent (W/V), followed by soy yeast. The resulting solution was incubated at 30°C. for 7 days to yield a liquid seasoning having a flavor which resembled closely to that of soy.

The aforesaid hydrolyzate solution was treated in the same manner as mentioned above and left standing at 30°C. for 7 days, except that seeded culture of the above-noted salt-resistant lactic acid bacterium was omitted. The resulted hydrolyzate solution showed a free amino acid ratio (AN/TN) not different from that of the clear hydrolyzate solution immediately after hydrolysis.

EXAMPLE 7

To a mixture of 10 g fish meal (produced by Taiyo Fishery Co.) and 10 g of wheat bran koji prepared with Aspergillus oryzae, was added 100 ml of tap water. After having been adjusted so as to contain 6.5 percent (W/V) of sodium chloride and further adjusted to pH 6.0, the mixture was subjected to hydrolysis at 45°C. for 17 hours while being stirred. After having been freed from insolubles, the hydrolyzate solution showed a total nitrogen (TN) of 0.85 percent (W/V) and a free amino acid ratio (AN/TN) of 0.36. To the hydrolyzate solution, were added cells of Tetracoccus soyae, FERM-P No. 1401 (ATCC 21787) so that the solution may contain $10^8$ cells per milliliter. The mixture was subjected to contacting treatment at 45°C. for 10 hours. After the treatment, the hydrolyzate solution showed a free amino acid ratio (AN/TN) of 0.45, the percentage increase in free amino acid content being 25.0 percent. The hydrolyzate solution was freed from insolubles and cells to yield a protein hydrolyzate having an excellent flavor.

The aforesaid hydrolyzate solution was treated in the same manner as mentioned above and stirred at 45°C. for 10 hours, except that the contact treatment with the above noted cells of the salt-resistant lactic acid bacterium was omitted. The resulting hydrolyzate solution showed a free amino acid ratio (AN/TN) not different from that of the hydrolyzate solution immediately after hydrolysis.

EXAMPLE 8

The procedure mentioned in Example 2 was followed except that Streptococcus lactis IFO 3434 was used in place of the Pediococcus soyae. The protein hydrolyzate obtained had a free amino acid ratio (AN/TN) of 0.47 and an excellent flavor, the percent increase in free amino acid content being 14.6 percent.

EXAMPLE 9

In 10 liters of tap water, was suspended 1 kg of defatted soy bean which had been subjected to thermal denaturation. To the suspension, were added 50 g of the proteolytic enzyme preparation used in Example 2 and cells of Pediococcus soyae IAM 1681 (ATCC 13622) which had been cultured in the same medium as that mentioned in Example 2, so that the suspension may contain $10^8$ cells per milliliter. The suspension was incubated at 40°C. for 4 days while being mildly stirred. The supernatant [TN = 0.7 % (W/V)] obtained by centrifuging the incubated suspension showed a free amino acid ratio (AN/TN) of 0.49 and proved to be a protein hydrolyzate excellent in flavor.

On the contrary, the hydrolyzate solution [TN = 0.7 % (W/V)], which was prepared in the same manner as mentioned above except that the cells of Pediococcus soyae were not added, showed a free amino acid ratio (AN/TN) of only 0.42.

What is claimed is:

1. In a process for producing a protein hydrolyzate from proteinaceous materials by hydrolysis with proteolytic enzymes in an aqueous medium to form a protein partial hydrolyzate containing polypeptides the improvement comprising inoculating and culturing salt-resistant lactic acid bacteria selected from the group consisting of Pediococcus halophilus, Pediococcus soyae, Tetracoccus soyae and Streptococcus thermophilus in the aqueous medium containing said protein partial hydrolyzate and up to 12 percent by weight of sodium chloride based on the volume of the aqueous medium until the free amino acid content in the aqueous medium is increased.

2. In a process for producing a protein hydrolyzate from proteinaceous material by hydrolysis with proteolytic enzymes in an aqueous medium to form a protein partial hydrolyzate containing polypeptides the improvements comprising adding cells of salt-resistant lactic acid bacteria selected from the group consisting of *Pediococcus halophilus*, *Pediococcus soyae*, *Tetracoccus soyae* and *Streptococcus thermophilius* to the aqueous medium containing said protein partial hydrolyzate and 0–12 percent by weight of sodium chloride based on the volume of the aqueous medium and allowing said bacteria to contact and break down the polypeptides to increase the free amino acid content of the hydrolyzate.

3. A process according to claim 1, wherein the inoculation and culture of the salt-resistant bacteria are conducted after substantial termination of the hydrolysis of proteinaceous materials.

4. A process according to claim 1, wherein the salt-resistant lactic acid bacteria are those which are resistant to sodium chloride in a concentration of 10 percent by weight based on a volume of an aqueous medium or higher.

5. A process according to claim 1, wherein the salt-resistant lactic acid bacteria are those selected from the group consisting of *Pediococcus halophilus* ATCC 21786, *Pediococcus soyae*, ATCC 13621, *Pediococcus soyae*, ATCC 13622, *Pediococcus soyae*, ATCC 13623, *Tetracoccus soyae* ATCC 21787, *Streptococcus thermophilus* IAM 1047, *Streptococcus thermophilus* and *Streptococcus thermophilus* ATCC 19282.

6. A process according to claim 1, wherein the culture of salt-resistant bacteria is conducted at a pH of 5 to 8 and at a temperature of 15° to 60°C. for 1 to 15 days.

7. A process according to claim 1, wherein the proteolytic enzyme is one member selected from the group consisting of enzymes produced by aspergilli, streptomyces, pepsin and papain.

8. A process according to claim 1, wherein the proteinaceous material is one member selected from the group consisting of soybean, wheat gluten, milk casein, fish meal, cattle meat and yeast.

9. A process according to claim 2, wherein the adding of the cells of salt-resistant bacteria is conducted at a pH of 5 to 8 and at a temperature of 15° to 60°C. for 10 to 72 hours.

10. A process according to claim 2, wherein the addition of the cells of said bacteria is conducted after substantial termination of the hydrolysis of proteinaceous materials.

11. A process according to claim 2, wherein the salt-resistant lactic acid bacteria are those which are resistant to sodium chloride in a concentration of 10 percent by weight based on a volume of an aqueous medium or higher.

12. A process according to claim 2, wherein the salt-resistant lactic acid bacteria are those selected from the group consisting of *Pediococcus halophilus* ATCC 21786, *Pediococcus soyae* ATCC 13621, *Pediococcus soyae* ATCC 13622, *Pediococcus soyae* ATCC 13623, *Tetracoccus soyae* ATCC 21787, *Streptococcus thermophilus* IAM 1047 and *Streptococcus thermophilus* ATCC 19282.

13. A process according to claim 2, wherein amount of the cells of salt-resistant lactic acid bacteria to be added is $10^8$ to $10^{10}$ in terms of number of cells per milliliter.

14. A process according to claim 2, wherein the proteolytic enzyme is a member selected from the group consisting of enzymes produced by aspergilli, streptomyces, pepsin and papain.

15. A process according to claim 2, wherein the proteinaceous material is one member selected from the group consisting of soybean, wheat gluten, milk casein, fish meal, cattle meat and yeast.

* * * * *